(12) United States Patent
Burdeniuc

(10) Patent No.: US 6,472,553 B1
(45) Date of Patent: Oct. 29, 2002

(54) SYNTHESIS OF NEW POLYNITRILES FROM CYCLOALPHATIC VICINAL PRIMARY DIAMINES

(75) Inventor: Juan Jesus Burdeniuc, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/123,929

(22) Filed: Apr. 17, 2002

Related U.S. Application Data

(62) Division of application No. 09/774,343, filed on Jan. 31, 2001.

(51) Int. Cl.$^7$ .............................................. C07C 255/05
(52) U.S. Cl. ...................................... 558/367; 558/430
(58) Field of Search ................................. 558/367, 430

(56) References Cited

U.S. PATENT DOCUMENTS

| | | | |
|---|---|---|---|
| 3,231,601 A | 1/1966 | Peterli ......................... | 260/465 |
| 3,496,213 A | 2/1970 | Ross .......................... | 260/465 |
| 4,153,567 A | 5/1979 | Kluger et al. ............ | 252/51.5 A |
| 4,321,354 A | 3/1982 | Kluger et al. ............... | 528/122 |
| 6,245,932 B1 * | 6/2001 | Burdeniuc et al. .......... | 558/367 |

* cited by examiner

*Primary Examiner*—Joseph K. McKane
*Assistant Examiner*—Golam M. M. Sjameem
(74) *Attorney, Agent, or Firm*—Mary E. Bongiorno

(57) ABSTRACT

Compounds of the structure:

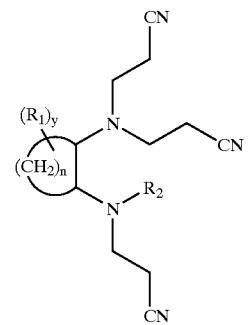

wherein $R_1$ is H, a C1 to C4 alkyl, or a substituted C1 to C4 alkyl; $R_2$ is H or a cyanoethyl; n is an integer of 1 to 4, and y is 1 or 2, and a method for making the compounds. The compounds are made by reacting acrylonitrile with one or more cycloaliphatic vicinal diamines in the presence of water and a catalytic amount of an acid catalyst having a $pK_a$ of −3.0 to 7.5.

8 Claims, No Drawings

SYNTHESIS OF NEW POLYNITRILES FROM CYCLOALPHATIC VICINAL PRIMARY DIAMINES

CROSS REFERENCE TO RELATED APPLICATIONS

This is a divisional of U.S. patent application Ser. No. 09/774,343, filed on Jan. 31, 2001, now allowed.

BACKGROUND OF THE INVENTION

Processes for the reaction of primary and secondary amines with acrylonitrile to form corresponding cyanoethylamines are known. The products that result from the cyanoethylation of organic amines are of industrial importance because they have broad utility in a variety of applications. For example, cyanoethylated amines can be used as coupling components in the preparation of azo dyes for paper and synthetic fibers. Also, the pendant nitrile groups can be reduced to the amine and thereby generate polyfunctional amines for use as epoxy and isocyanate curatives.

In general, amines are more reactive with acrylonitrile than many other classes of organic compounds, but the ease of the addition among amines varies considerably. For example, primary amines having two active hydrogen atoms can add one or two acrylonitrile molecules. Addition of the first acrylonitrile molecule to a primary amine may occur at relatively low temperature while addition of the second acrylonitrile may require heating and the use of more rigorous conditions. Stereochemistry between primary and secondary amines and the complexity of the amine also affect the rate of addition of acrylonitrile to the amine.

The following patents represent processes for the cyanoethylation of primary and secondary amines:

U.S. Pat. No. 3,231,601 (Peterli, 1966) discloses the cyanoethylation of aromatic amines in good yield by carrying out the reaction in an aqueous medium, i.e. water as the sole solvent, and in the presence of salts of aromatic amines and strong acids as catalysts. Examples of strong acids suited for the reaction include sulfuric, phosphoric, hydrochloric, p-toluene sulfonic, and trifluoroacetic.

U.S. Pat. No. 3,496,213 (Ross, 1970) discloses the mono-N-cyanoethylation of aromatic amines by reacting the aromatic amine with acrylonitrile in the presence of zinc chloride carried in an aqueous reaction medium.

U.S. Pat. No. 4,153,567 (Kluger et al., 1979) discloses a process for producing additives for lubricants and fuel which are based on the reaction of the acrylonitrile and vicinal cyclohexanediamine followed by reaction with a heterocyclic imide. In the process, cyanoethylation is effected by reacting 1,2 diaminocyclohexane with acrylonitrile in the presence of an acid catalyst. One and two moles of acrylonitrile are reacted with the vicinal cyclohexylamine to give both the monocyanoethylated product, i.e., N-(2-cyanoethyl)1,2-diaminocyclohexane and the dicyanoethylated product, i.e., N,N'-di-(2-cyanoethyl)-1,2-diaminocyclohexane. Examples of suitable acid catalysts for the reactions are reported to be p-toluene-sulfonic acid and acetic acid salts. It is also reported that, following cyanoethylation, the nitrile can be reduced to the amine by a catalytic hydrogenation using Raney nickel or other transition metals as catalysts.

U.S. Pat. No. 4,321,354 (Kluger et al., 1982) discloses the production of cycloaliphatic polyamines, particularly the polyamine derived from 1,2-diaminocyclohexane. As in —567, 1,2-diaminocyclohexane is reacted with one or two moles acrylonitrile respectively in the presence of an acetic acid catalyst. The resultant cyanoethylated diaminocyclohexanes can be reduced with hydrogen to form the polyfunctional amines.

A method of cyanoethylation of substituted cycloaliphatic vicinal primary amines to produce a compound with three or four amine substitutions has not been shown.

BRIEF SUMMARY OF THE INVENTION

This invention is directed to new compounds represented by the structural formula below and to the method of making the compounds.

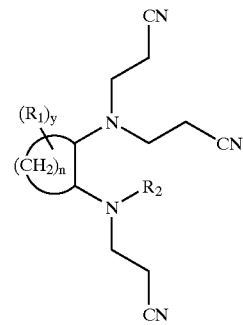

$R_1$ represents H, C1 to C4 alkyl, or substituted C1 to C4 alkyl; $R_2$ represents H or a cyanoethyl; n is an integer of 1 to 6, and y is 1 or 2. In preferred compounds, n is 4, y is 1, $R_1$ is methyl, and $R_2$ is H or a cyanoethyl.

The compounds are produced by cyanoethylation of a cycloaliphatic vicinal diamine in the presence of water and a catalytic amount of an acid having a pKa of −3 to 7.5, preferably acetic acid. The use of a catalytic amount of an acid and water results in:

production of heretofore unknown products in good yield;

production of little or no unwanted byproducts; and ability to immediately hydrogenate the polynitriles to polyamines without separation and/or purification of the products.

In a preferred method of making the compounds of this invention, and for purposes of illustration, o-methylcyclohexyldiamines ($H_6OTD$) can be reacted with acrylonitrile in the presence of a stoichiometric amount of water and a catalytic amount of acetic acid to produce three products of structures A, B, and C (shown below), with little or no unwanted byproducts.

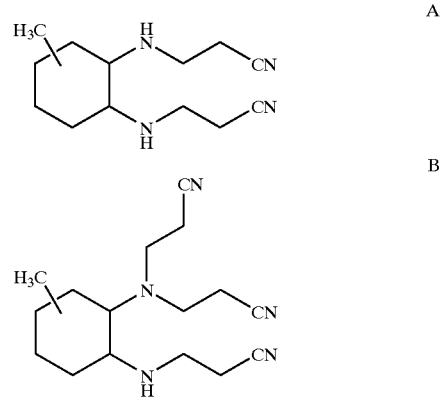

-continued

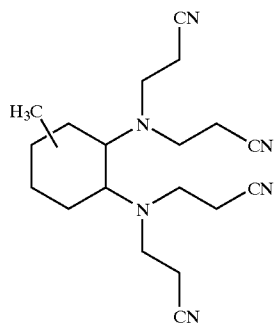

C

DETAILED DESCRIPTION OF THE INVENTION

In the method of making the novel compounds of this invention, acrylonitrile is reacted with a cycloaliphatic vicinal diamine, in an amount water equivalent to the diamine and a catalytic amount of an acid having a $pK_a$ of −3 to 7.5, to produce a product of general structure I below:

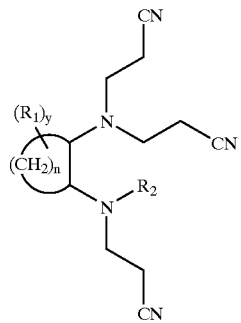

$R_1$ represents H, C1 to C4 alkyl, such as methyl, ethyl, propyl, isopropyl, butyl, and t-butyl, or substituted C1 to C4 alkyl, wherein the substitution can be hydroxalkyl, carboxylic acid, amide, and amino; $R_2$ represents H or a cyanoethyl; n is an integer of 1 to 6, and y is 1 or 2. In preferred compounds, n is 4, y is 1, $R_1$ is methyl, and $R_2$ is H or a cyanoethyl.

In the current method, one mole of acrylonitrile is reacted with one equivalent of of one or more cycloaliphatic vicinal diamines, in the presence of water and a catalytic amount of an acid having a $pK_a$ of −3 to 7.5; preferably 1 to 6. The molar concentration of water per mole of cycloaliphatic diamine can range from 0.1 to 10:1, preferably from about 1:1 to 2:1.

Examples of cycloaliphatic vicinal diamines commonly used in the cyanoethylation process are 1,2-diaminocyclohexane; 1-methyl-2,3-diaminocyclohexane, 1-methyl-3,4-diaminocylcohexane, a mixture of 1-methyl-2,3-diaminocyclohexane and 1-methyl-3,4-daiminocyclohexane, t-butyldiaminocylcohexane, ethyldiaminocylcohexane, and isopropyldiaminocyclohexane.

By catalytic amount of acid is meant an amount which will noticeably increase the rate of reaction. Typically the amount of catalyst ranges from 0.1 to 1.0 mole per mole of cycloaliphatic diamine. Acetic acid is the preferred acid.

The temperature for effecting the reaction between acrylonitrile and the cycloaliphatic vicinal amine generally ranges from about 25 to 150° C., preferably 50 to 80° C.

Pressure for the reaction can range from atmospheric to 60 psig. Atmospheric pressure is preferred.

The combination of water and acid unexpectedly leads to a product containing substantial amounts of compounds having 3 and 4 cyanoethyl substitutions on the amine nitrogens and little or no byproducts.

The product of the cyanoethylation reaction can be used in a catalytic hydrogenation reaction without purifying or separating the product.

The invention will be further clarified by a consideration of the following examples, which are intended to be purely exemplary of the invention.

EXAMPLE 1

CYANOETHYLATION OF $H_6OTD$ WITH ACRYLONITRILE IN THE PRESENCE OF A STOICHIOMETRIC AMOUNT OF ACETIC ACID

In this example acrylonitrile was refluxed with $H_6OTD$ (a mixture composed of 35% 2,3-diaminomethylhexane and 65% 3,4-diaminomethylhexane) for 24 hours in the presence of a stoichiometric amount of acetic acid and with no added water.

In a 250 ml three-necked flask equipped with a magnetic stir bar, oil bath, reflux condenser, and dropping funnel, was placed 30.90 g (0.24 mole) of $H_6OTD$ together with 28.96 g (0.48 mole) of acetic acid. The flask was heated to 70° C. and 62.10 g of acrylonitrile (1.17 mole) was added dropwise. The temperature was controlled by the rate of addition of acrylonitrile so that it did not exceed 77° C. The addition was finished in about 20 minutes and refluxed was continued for 24 hours. Analysis of a sample by GCMS, Solid Probe-Mass Spectroscopy and Chemical Ionization Mass Spectroscopy with $NH_3$ and $ND_3$ showed the following compounds:

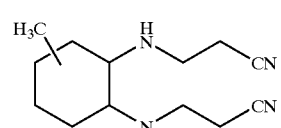

A

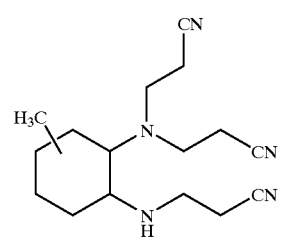

B

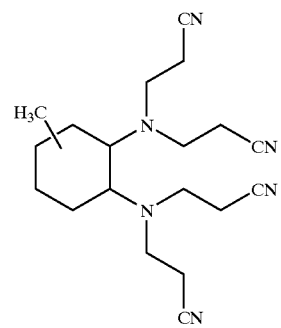

C

-continued

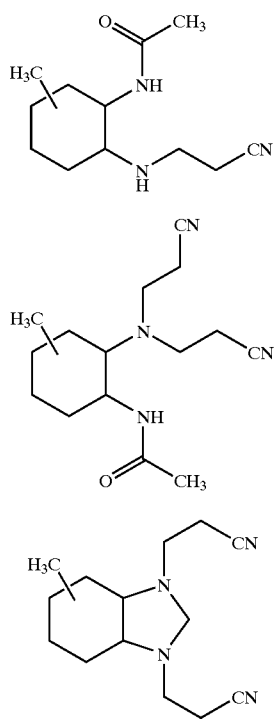

The % GC area for these compounds is listed in the following table:

| Product | % GC Area |
|---|---|
| A | 14.40 |
| B | 33.95 |
| C | 2.93 |
| D | 4.60 |
| E | 33.80 |
| F | 2.65 |

This example shows that, in the presence of a stoichiometric amount of acetic acid, an acceptable yield for B can be obtained (33.95%). However, the diamine can also react with acetic acid to form amides and other byproducts; thus, decreasing the yields for the desired products B and C.

EXAMPLE 2

CYANOETHYLATION OF H$_6$OTD WITH ACRYLONITRILE IN THE ABSENCE OF AN ACID CATALYST

In this example, acrylonitrile was reacted with H$_6$OTD containing 25% water in the absence of acid catalyst In a 250 ml three-necked flask equipped with a magnetic stir bar, oil bath, reflux condenser, and dropping funnel, were placed 30.90 g (0.24 mole) of 1,2-diaminomethyl-cyclohexanes and 7.7 g (0.42 mole) of water. The reaction vessel was heated up to 70° C. and 32 g of acrylonitrile (0.6 mole) was added dropwise. An exotherm occurred and the temperature was controlled during the addition so that it did not exceed 77° C. The addition of acrylonitrile was completed in about 20 minutes. Once the addition was finished, refluxed was continued for 18 hours. A sample was analyzed (by GCMS, Solid Probe-Mass Spectroscopy and Chemical Ionization Mass Spectroscopy with NH$_3$ and ND$_3$) showing product A (M$^+$=234) (93%) and B (M+=7%).

In this example a much smaller amount of B was obtained than in Example 1; however no byproducts D, E and F were formed.

EXAMPLE 3

CYANOETHYLATION OF H$_6$OTD WITH ACRYLONITRILE IN THE PRESENCE OF STOICHIOMETRIC AMOUNTS OF ACETIC ACID AND ADDED WATER

In this example, acrylonitrile was reacted with H$_6$OTD containing 25% water in the presence of a stoichiometric amount of acetic acid.

In a 250 ml three-necked flask equipped with a magnetic stir bar, oil bath, reflux condenser, and dropping funnel, were placed 30.90 g (0.24 mole) of 1,2-diaminomethyl-cyclohexanes, 7.7 g (0.42 mole) of water and 28.8 g (0.48 mole) of acetic acid. The reaction vessel was heated to 70° C. and 62.1 g of acrylonitrile (1.17 mole) was added dropwise. An exotherm occurred and the temperature was controlled during the addition so that it did not exceed 77° C. The addition of acrylonitrile was completed in about 20 minutes and the mixture was refluxed for 24 hours. Analyses by GCMS, Solid Probe-Mass Spectroscopy and Chemical Ionization Mass Spectroscopy using NH$_3$ and ND$_3$, were consistent with the presence of the same products as described in Example 2. The % GC area for each compound is shown below:

| Product | % GC Area |
|---|---|
| A | 25.48 |
| B | 56.20 |
| C | 1.78 |
| D | 1.04 |
| E | 1.17 |
| F | 9.12 |

This data shows that the addition of water decreased the amount of by-products D, E and F from a total of ~41% (Example 1) to a total of ~11.3%. Also, the yield of product B (56.20 %) significantly increased, compared to Example 1 where only 33.95% could be made.

EXAMPLE 4

CYANOETHYLATION OF H$_6$OTD WITH ACRYLONITRILE IN THE PRESENCE OF A CATALYTIC AMOUNT OF ACETIC ACID AND ADDED WATER

This example shows the results obtained when catalytic amounts of acetic acid were used. In a 250 ml three-necked flask equipped with a magnetic stir bar, oil bath, reflux condenser, and dropping funnel, were placed 30.40 g (0.24 mole) of 1,2-diaminomethylcyclo-hexanes, 10 g (0.55 mole) of water and 3.63 g (0.068 mole) of acetic acid. The reaction vessel was heated up to 70° C. and 67.5 g of acrylonitrile (1.27 mole) was added dropwise so that the temperature did not exceed 77° C. The addition of acrylonitrile was completed in about 20 minutes and the mixture was refluxed for 72 hours. GCMS, Solid Probe-Mass Spectroscopy and Chemical Ionization Mass Spectroscopy with NH$_3$ and ND$_3$ showed A, B and C. The GC analysis is shown in the following table:

| Product | % GC Area |
|---|---|
| A | 21 |
| B | 64 |
| C | 15 |

These results show that water and catalytic amounts of acids can give good yields of the desired products B and C without the formation of undesired byproducts resulting from the reaction between acetic acid and the vicinal diamine.

EXAMPLE 5

CYANOETHYLATION OF PRODUCT A TO FORM PRODUCTS B AND C USING A CATALYTIC AMOUNT OF ACETIC ACID IN THE PRESENCE OF ADDED WATER

In this example, acrylonitrile was reacted with product A to see if yields of can be further improved.

In a 250 ml three-necked flask equipped with a magnetic stir bar, oil bath, reflux condenser, and dropping funnel, were placed 47.75 g (0.20 mole) of B, 10.0 g (0.55 mole) of water and 3.62 g (0.060 mole) of acetic acid. The reaction vessel was heated to 70° C. and 32.4 g of acrylonitrile (0.61 mole) was added dropwise with the temperature not surpassing 77° C. The addition of acrylonitrile was completed in about 10 minutes. Once the addition was finished, a sample was analyzed by GCMS, Solid Probe-Mass Spectroscopy and Chemical Ionization Mass Spectroscopy with $NH_3$ and $ND_3$.

| Product | % GC Area |
|---|---|
| A | 22 |
| B | 61 |
| C | 17 |

In this case, no significant improvement in the yields of B and C could be accomplished when A was used as a substrate for cyanoethylation.

EXAMPLE 6

CYANOETHYLATION OF $H_6OTD$ WITH ACRYLONITRILE IN THE PRESENCE OF WATER CATALYZED BY p-TOLUENESULFONIC ACID

This experiment shows that using a stronger acid, such as p-toluenesulfonic acid, does not improve the yield on the desired products. In fact, the yields obtained with an acid stronger than acetic acid were lower.

In a 250 ml three-necked flask equipped with a magnetic stir bar, oil bath, reflux condenser, and dropping funnel, were placed 30.90 g (0.24 mole) of 1,2-diaminomethylcyclohexanes, 7.7 g (0.42 mole) of water and 7.56 g (0.040 mole) of p-toluenesulfonic acid monohydrate. The reaction vessel was heated to 70° C. and 62.10 g of acrylonitrile (1.17 mole) was added dropwise. A mild exotherm occurred and the temperature was controlled during the addition so that it did not exceed 77° C. The addition of acrylonitrile was completed in about 20 minutes. After that, the reaction mixture was heated under reflux for 72 hours. Compounds were analyzed by GCMS, Solid Probe-Mass Spectroscopy and Chemical Ionization Mass Spectroscopy with $NH_3$ and $ND_3$.

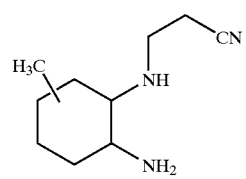

G

The % GC area are shown in the table below:

| Product | % GC Area |
|---|---|
| A | 38.5 |
| B | 40.9 |
| C | 7.9 |
| G | 10.0 |

Comparing these results with those obtained in Example 4, p-toluenesulfonic acid was not as effective a catalyst for this reaction as acetic acid.

EXAMPLE 7

CYANOETHYLATION OF $H_6OTD$ WITH ACRYLONITRILE IN THE PRESENCE OF WATER CATALYZED BY PHOSPHORIC ACID-MONOSODIUM SALT

This experiment shows the results obtained when using an inorganic acid such as phosphoric acid monosodium salt ($NaH_2PO_4$).

In a 250 ml three-necked flask equipped with a magnetic stir bar, oil bath, reflux condenser, and dropping funnel, were placed 30.90 g (0.24 mole) of 1,2-diaminomethyl-cyclohexanes, 20 g (1.11 mole) of water and 10 g (0.083 mole) of $NaH_2PO_4$. The reaction vessel was heated up to 70° C. and 62.10 g of acrylonitrile (1.17 mole) was added dropwise. A exotherm occurred and the temperature was controlled during the addition so that it did not exceed 77° C. The addition of acrylonitrile was completed in about 20 minutes. After that, the reaction mixture was heated under reflux for 48 hours. The resulting amber oil mixture was analyzed and its composition corresponded to a mixture of A (59.3%), B (34.6 %), and C (0.4%). These results show that $NaH_2PO_4$ was not as effective as acetic acid and it was even less effective than p-toluenesulfonic acid in its ability to catalyze the condensation of the diamine with acrylonitrile to form good yields of B and C.

EXAMPLE 8

CYANOETHYLATION OF $H_6OTD$ WITH ACRYLONITRILE IN THE PRESENCE OF WATER CATALYZED BY PHOSPHORIC ACID-DISODIUM SALT

This experiment shows the results obtained when using an even weaker inorganic acid, phosphoric acid disodium salt ($Na_2HPO_4$).

In a 250 ml three necked flask equipped with a magnetic stir bar, oil bath, reflux condenser, and dropping funnel, were placed 30.90 g (0.24 mole) of 1,2-diaminomethylcyclohexanes, 7.7 g (0.42 mole) of water and 10 g (0.070 mole) of Na$_2$HPO$_4$. The reaction vessel was heated up to 70° C. and 62.10 g of acrylonitrile (1.17 mole) was added dropwise. A exotherm occurred and the temperature was controlled during the addition so that it did not exceed 77° C. The addition of acrylonitrile was completed in about 20 minutes. After that, the reaction mixture was heated under reflux for 48 hours. The resulting amber oil mixture was analyzed and its composition corresponded to a mixture of A (93%), B (7%), and no C detected. By comparing these results with those obtained in Example 2, it can be concluded that Na$_2$HPO$_4$ is not an effective catalyst for the condensation of the diamine with acrylonitrile to form good yields of B and C.

EXAMPLE 9

ACID CATALYST EFFICIENCY AND pK$_a$

The data in the following table show that acids with a pK$_a$ comparable to that of acetic acid will be the best catalysts for the Michael condensation between substituted cycloaliphatic vicinal primary amines and acrylonitrile and consequently they will give the best yields of B and C.

| Product | Acid Catalyst | | | | | |
|---|---|---|---|---|---|---|
| | Na$_2$HPO4 pK$_a$ = 12.32 0.3$^d$ | NaH$_2$PO$_4$ pK$_a$ = 7.21 0.34$^d$ | p-Toluene sulfonic acid pK$_a$ = −2.7 0.16$^d$ | Acetic Acid$^a$ pK$_a$ = 4.75 2.0$^d$ | Acetic Acid$^b$ pK$_a$ = 4.75 2.0$^d$ | Acetic Acid$^c$ pK$_a$ = 4.75 2.8$^d$ |
| % A | 93.0 | 59.3 | 38.5 | 15.0 | 25.5 | 21.0 |
| % B | 7.0 | 34.6 | 40.9 | 34.0 | 56.2 | 64.0 |
| % C | 0.0 | 0.4 | 7.9 | 3.0 | 1.78 | 15.0 |
| % D | 0.0 | 0.0 | 0.0 | 4.6 | 1.04 | 0.0 |
| % E | 0.0 | 0.0 | 0.0 | 34.0 | 1.2 | 0.0 |
| % F | 0.0 | 0.0 | 0.0 | 2.7 | 9.1 | 0.0 |
| % G | 0.0 | 0.0 | 10.0 | 0.0 | 0.0 | 0.0 |
| % Un-knowns | 0.0 | 5.7 | 2.7 | 6.7 | 5.18 | 0.0 |

$^a$Stoichiometric amount of acetic acid.
$^b$Stoichiometric amount of acetic acid in the presence of added water.
$^c$Catalytic amount of aqueous acetic acid.
$^d$Mole of acid catalyst per mole of vicinal diamine.

EXAMPLE 10

CATALYTIC HYDROGENATION OF POLYNITRILES TO POLYAMINES USING A RANEY COBALT CATALYST

This example shows that hydrogenation of polynitriles can be carried out using a catalyst such as raney-cobalt.

The starting sample contained the following compounds: N,N'-bis-(2-cyanoethyl)-1,2-diaminomethylcyclohexane (~25.5%), N,N,N'-tris-(2-cyanoethyl)-1,2-diaminomethylcyclohexane (56.20%) and N,N,N',N',-tetra-(2-cyanoethyl)-1,2-diaminomethylcyclohexane (5.2%). This mixture (12.93 g) was dissolved in 116 g of isopropanol and hydrogenated in a semi batch process in a 300 ml Hastalloy reactor. The reactor contained 1.07 g of Raney 2724 cobalt catalyst purchased from Davison Chemical, 56.3 g of isopropanol and hydrogen (850 psi). The mechanical stirrer was set at 310 rpm and the temperature was 120° C. The solution was slowly fed into the reactor at 13 ml/hour (total time=12 hours). The isopropanol solution was removed from the reactor and distilled off to give a crude amine product containing: 40% of N,N'-di-(3-aminopropyl)-1,2-diaminomethylcyclohexane (H), 37% of N,N,N'-tri-(3-aminopropyl)-1,2-diaminomethylcyclohexane (I) and 5% of N,N,N',N'-tris-(3-aminopropyl)-1,2-diaminomethylcyclohexane (J) as determined by GCMS, Solid Probe-Mass Spectroscopy and Chemical Ionization Mass Spectroscopy with NH$_3$ and ND$_3$. Analysis showed the following molecular ion peaks: 242 (M$^+$ for H); 299(M$^+$ for I) and; 356(M$^+$ for J).

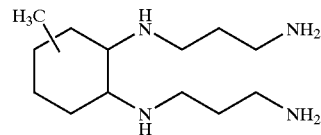

H

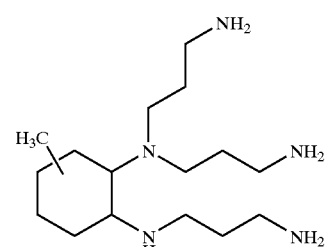

I

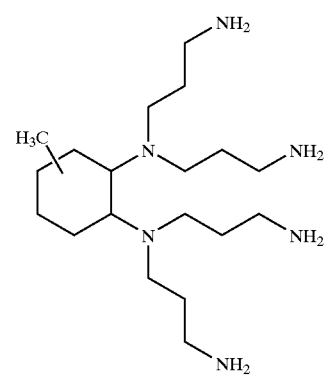

J

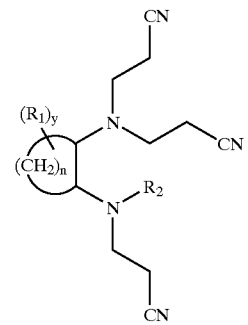

What is claimed is:
1. A method for making compounds of the structure:

wherein R$_1$ is H, a C1 to C4 alkyl, or a substituted C1 to C4 alkyl; R$_2$ is H or a cyanoethyl; n is an integer of 1 to 4, and y is 1 or 2, comprising reacting acrylonitrile with one or more cycloaliphatic vicinal diamines in the presence of water and a catalytic amount of an acid catalyst having a pK$_a$ of −3.0 to 7.5.

2. The method of claim 1 wherein n is 4, y is 1, $R_1$ is methyl, and $R_2$ is H or a cyanoethyl.

3. The method of claim 1 wherein the $pK_a$ of the acid catalyst ranges from 1 to 6.

4. The method of claim 1 wherein the acid catalyst is acetic acid.

5. The method of claim 1 wherein the one or more cycloaliphatic vicinal diamines is 1-methyl-2,3-diaminocyclohexane and/or 1-methyl-3,4-diaminocylcohexane.

6. The method of claim 1 wherein water is present in a ratio of 0.1 to 10 moles water per mole of cycloaliphatic vicinal diamine.

7. The method of claim 1 wherein a temperature of 60 to 80° C. is used.

8. The method of claim 1 wherein the product of the reaction is used directly in a catalytic hydrogenation reaction.

* * * * *

UNITED STATES PATENT AND TRADEMARK OFFICE
CERTIFICATE OF CORRECTION

PATENT NO.   : 6,472,553 B1
DATED        : October 29, 2002
INVENTOR(S)  : Juan Jesus Burdeniuc It is certified that error appears in the above-identified patent and that said Letters Patent is hereby corrected as shown below:

Column 10,
Line 45, move the formula

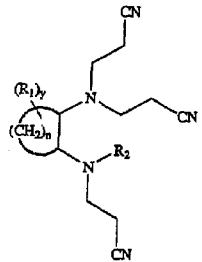

and insert it after the words in Column 10, line 59, "1. A method for making compounds of the structure:"

Signed and Sealed this

Twenty-fifth Day of February, 2003

JAMES E. ROGAN
*Director of the United States Patent and Trademark Office*